United States Patent
Luckenbach et al.

(10) Patent No.: US 10,932,894 B2
(45) Date of Patent: Mar. 2, 2021

(54) ANIMAL BACK BRACE

(71) Applicant: WiggleLess, LLC, Ojai, CA (US)

(72) Inventors: David Luckenbach, Ojai, CA (US); Lisa Luckenbach, Ojai, CA (US)

(73) Assignee: WIGGLELESS, LLC, Ojai, CA (US)

( * ) Notice: Subject to any disclaimer, the term of this patent is extended or adjusted under 35 U.S.C. 154(b) by 198 days.

(21) Appl. No.: 15/949,478

(22) Filed: Apr. 10, 2018

(65) Prior Publication Data

US 2019/0307541 A1    Oct. 10, 2019

(51) Int. Cl.
*A61F 5/02*  (2006.01)
*A61D 9/00*  (2006.01)

(52) U.S. Cl.
CPC . *A61D 9/00* (2013.01); *A61F 5/02* (2013.01)

(58) Field of Classification Search
CPC ... A61D 9/00; A61F 5/02; A61F 5/028; A61F 5/03; A01K 13/006
USPC ............... 602/19; 119/814, 856, 863, 850
See application file for complete search history.

(56) References Cited

U.S. PATENT DOCUMENTS

| | | | |
|---|---|---|---|
| D312,151 S | 11/1990 | Dickey | |
| 5,226,874 A * | 7/1993 | Heinz | A61F 5/028 602/19 |
| D363,572 S | 10/1995 | Obenchain | |
| 5,896,831 A | 4/1999 | Alpert | |
| 5,941,199 A | 8/1999 | Tamura | |
| 5,996,537 A | 12/1999 | Caditz | |
| 6,267,083 B1 * | 7/2001 | Chimienti | A01K 13/006 119/850 |
| 6,601,540 B1 | 8/2003 | Davis | |
| 6,880,489 B2 | 4/2005 | Hartmann et al. | |
| 6,912,976 B2 | 7/2005 | Everett | |
| 6,976,453 B2 | 12/2005 | Goudal | |
| 7,370,608 B1 | 5/2008 | Friedman | |
| D585,606 S | 1/2009 | Kennedy | |
| 8,015,947 B2 | 9/2011 | Arreola | |
| D653,409 S | 1/2012 | Elliott | |
| D673,738 S | 1/2013 | Lanzendorf | |
| 9,107,388 B2 | 8/2015 | Howell | |
| D802,854 S | 11/2017 | Caruso | |
| 9,820,471 B2 | 11/2017 | Sebo | |
| 2006/0282032 A1 * | 12/2006 | Smith | A61F 5/026 602/19 |
| 2012/0316484 A1 | 12/2012 | Brannon et al. | |
| 2015/0034021 A1 | 2/2015 | Vogt | |
| 2016/0015003 A1 * | 1/2016 | Watson | A01K 1/0263 224/600 |

(Continued)

FOREIGN PATENT DOCUMENTS

DE        20021256 U1    5/2001

*Primary Examiner* — Rachael E Bredefeld
*Assistant Examiner* — Camtu T Nguyen
(74) *Attorney, Agent, or Firm* — Taft Stettinius & Hollister LLP (57) ABSTRACT

The invention relates to a brace for use with animals. The brace comprises an upper structure, a lower structure, a first reinforcement positioned to a first lateral side of a longitudinal axis of the upper structure, and a second reinforcement positioned to a second lateral side of the longitudinal axis of the upper structure. Each of the first reinforcement and second reinforcement are integral to the upper structure and parallel to the longitudinal axis. The lower structure is independent of and releasably secured to the upper structure.

18 Claims, 8 Drawing Sheets

(56) References Cited

U.S. PATENT DOCUMENTS

2017/0354530 A1\* 12/2017 Shagdar ............ A41D 13/0525

\* cited by examiner

ANIMAL BACK BRACE

BACKGROUND

Examples described herein relate generally to structures. More particularly, this invention is directed to a back brace for an animal.

DESCRIPTION OF THE RELATED ART

A domestic animal, such as a dog, may experience an injury during its life. The injury could be the result of an encounter with a larger animal, a fall, growing older, or the like. If the injury affects the spine of the animal, it is often challenging to foster and support recovery from the injury while simultaneously limiting unnecessary components that may further injure the animal or aggravate the existing injury. For example, existing back braces may include leg straps. Leg straps require an individual to position the straps around the dog's legs to secure the brace to the dog. Other braces may include non-flexible components arranged along the site of the injury. This could prevent a full recovery. Accordingly, there is a need for an improved animal back brace to better foster and support recovery from the injury while simultaneously limiting unnecessary components that may further injure the animal or aggravate the existing injury.

SUMMARY

Particular examples of the invention comprise a brace. Certain examples of the brace comprise an upper structure. The upper structure has a length extending from a first longitudinal extent to a second longitudinal extent along a longitudinal axis. The upper structure also has a width extending from a first lateral extent to a second lateral extent.

The brace further comprises a lower structure. The lower structure is independent of the upper structure and is releasably secured to the upper structure.

The brace further comprises a first reinforcement positioned to a first lateral side of the longitudinal axis and a second reinforcement positioned to a second lateral side of the longitudinal axis. The first reinforcement and the second reinforcement are integral to the upper structure. The first reinforcement and the second reinforcement are also parallel to the longitudinal axis.

The foregoing and other examples, objects, features, and advantages of the invention will be apparent from the following more detailed descriptions of particular examples of the invention, as illustrated in the accompanying drawings wherein like reference numbers represent like parts of the examples.

DETAILED DESCRIPTION OF THE INVENTION

Figure 1:
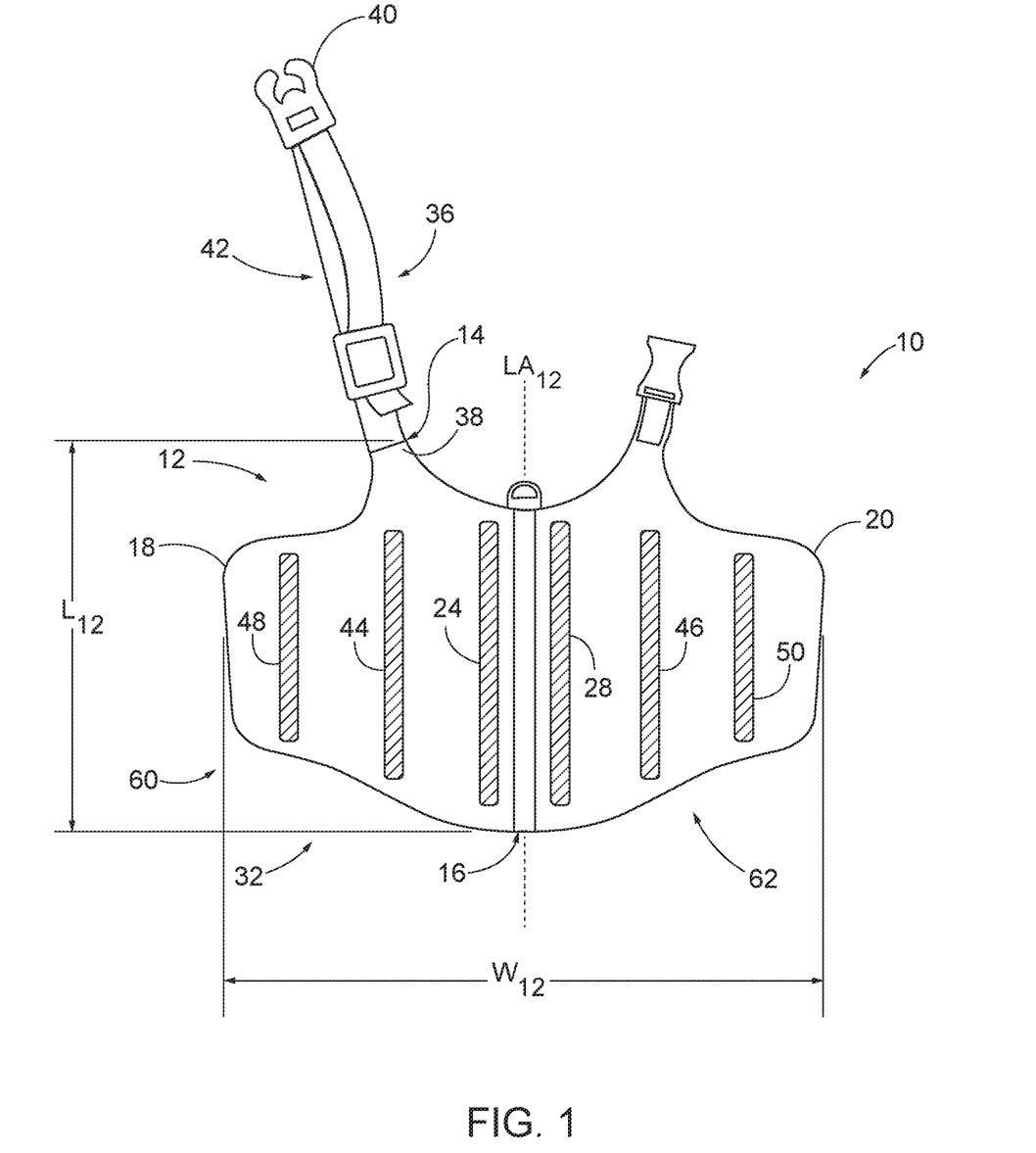
FIG. 1 is a top view of an upper structure of a back brace, in accordance with an example.
Figure 2:
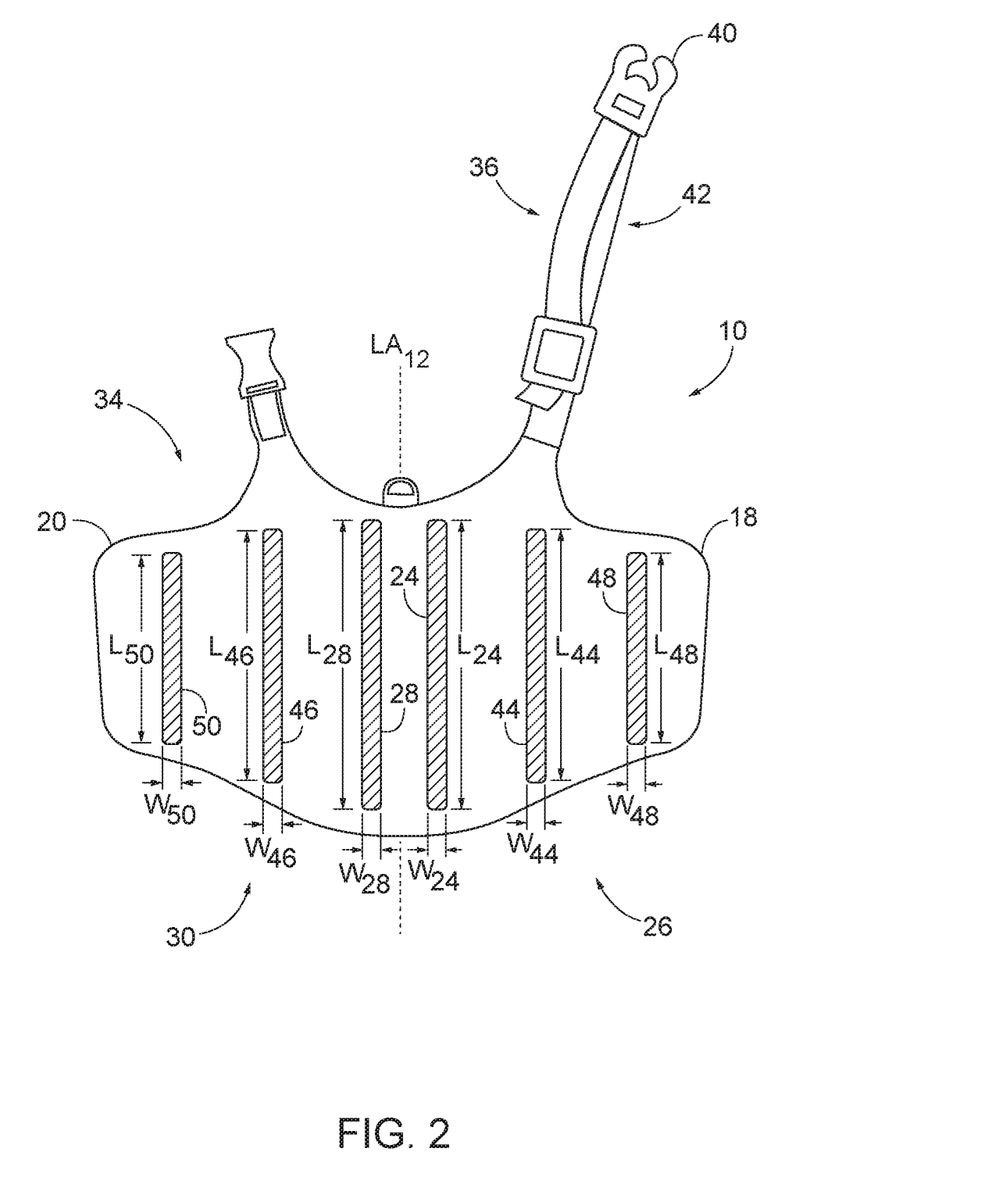
FIG. 2 is a bottom view of the upper structure of a back brace, in accordance with an example.

As illustrated in the figures, examples of the invention comprise a brace 10 and, more specifically, an animal back brace. As illustrated in FIG. 1, the brace 10 comprises an upper structure 12, which has a length $L_{12}$ extending from a first longitudinal extent 14 to a second longitudinal extent 16 along a longitudinal axis $LA_{12}$ of the upper structure 12. The upper structure 12 also has a width $W_{12}$ extending from a first lateral extent 18 to a second lateral extent 20. The brace 10 further comprises a lower structure 22 that is both independent of the upper structure 12 and releasably secured to the upper structure 12. As the lower structure is independent of and releasably secured to the upper structure, each of the lower structure and upper structure are not permanently affixed to each other. The brace 10 further comprises a first reinforcement 24 positioned to a first lateral side 26 of the longitudinal axis $LA_{12}$ of the upper structure 12 and a second reinforcement 28 positioned to a second lateral side 30 of the longitudinal axis $LA_{12}$ of the upper structure 12. The first reinforcement 24 and the second reinforcement 28 are integral to the upper structure 12. As used herein, "integral to" means "belonging as a part of the whole" meaning that the first reinforcement 24 and the second reinforcement 28 belong to the upper structure 12 as a part of the whole upper structure 12 (i.e., within the footprint or perimeter of the upper structure 12) as shown in FIGS. 1 and 2. In some examples, each of the reinforcements 24, 28 is disposed within the upper structure 12 such that the reinforcements 24, 28 may not be accessed outside of the upper structure 12. The first reinforcement 24 and the second reinforcement 28 are also parallel to the longitudinal axis $LA_{12}$. In some examples, the first reinforcement and the second reinforcement are both comprised of a rigid material such that neither the first reinforcement nor the second reinforcement are capable of being bent. In some examples, the first reinforcement and the second reinforcement are both comprised of a flexible material such that each of the first reinforcement and the second reinforcement are capable of being bent while still providing a reinforcing effect. In some examples, the first reinforcement is comprised of a first material. Additionally or alternatively, the second reinforcement is comprised of a second material that is either the same as the first material of the first reinforcement or different than the first material of the first reinforcement.

As shown in FIG. 1, the upper structure 12 further comprises a top side 32. The top side 32 comprises a breathable material and a connecting material to which the lower structure 22 is releasably secured. In some examples, the breathable material is a layer of mesh or a layer of knit fabric. Additionally or alternatively, the breathable material may comprise a combination of two or more materials, such as mesh or knit fabric. In some examples, the connecting material is an adhesive material or a hook and loop material (such as Velcro®). Additionally or alternatively, the connecting material may comprise a combination of two or more materials, such as a combination of adhesive material and a hook and loop material.

As shown in FIG. 2, the upper structure 12 further comprises a bottom side 34, and the bottom side 34 comprises a breathable material. In some examples, the breathable material is a layer of mesh or a layer of knit fabric. Additionally or alternatively, the breathable material may comprise a combination of two or more materials, such as mesh or knit fabric. In some examples, the breathable material on the bottom side of the upper structure is the same as the breathable material on the top side of the upper structure, but in some examples, the breathable material on the bottom side of the upper structure is different than the breathable material on the top side of the upper structure. In some examples, the upper structure comprises a single layer of breathable material, with one side of the breathable material forming the top side of the upper structure and the other side of the breathable material forming the bottom side of the upper structure. In other examples, the upper structure comprises more than one layer of breathable material, with one layer forming the top side of the upper structure and another layer forming the bottom side of the upper structure. In examples in which the upper structure comprises more than one layer of breathable material, the different layers may be attached to each other via stitching, adhesives, or other structure suitable for attachment.

As shown in FIGS. 1 and 2, the upper structure 12 further comprises a bracing component 36. The bracing component 36 comprises a first end 38 and a second end 40, and the first end 38 extends from the first lateral side 26 of the longitudinal axis $LA_{12}$ of the upper structure 12. The second end 40 is releasably secured to the second lateral side 30 of the longitudinal axis $LA_{12}$ of the upper structure 12. In some examples, the second end is releasably secured to the second lateral side of the longitudinal axis through use of a buckle with male and female ends. In other examples, the second end is releasably secured to the second lateral side of the longitudinal axis through use of an adhesive material, a hook and loop material, a clasp, a clamp, or other structure suitable for releasable security.

In some examples, the bracing component further comprises an adjustable attachment component 42, as shown in FIGS. 1 and 2. The adjustable attachment component 42 allows the bracing component to accommodate a variety of sizes of an animal such that a single brace may comfortably fit many animals. In some examples, the adjustable attachment component is a buckle and slider arrangement. Additionally or alternatively, the adjustable attachment component may further comprise a different structure for adjustment, such as a clasp and chain or the like.

As illustrated in FIGS. 1 and 2, the brace 10 further comprises a third reinforcement 44 positioned laterally outward relative the first reinforcement 24 and the longitudinal axis $LA_{12}$ and a fourth reinforcement 46 positioned laterally outward relative the second reinforcement 28 and the longitudinal axis $LA_{12}$. Each of the third reinforcement 44 and the fourth reinforcement 46 are integral to the upper structure 12 and parallel to the longitudinal axis $LA_{12}$. Additionally or alternatively, the third reinforcement 44 is separate from the first reinforcement 24, and the fourth reinforcement 46 is separate from the second reinforcement 28 such that each of the first reinforcement 24 and third reinforcement 44 are not in contact with each other and that each of the second reinforcement 28 and fourth reinforcement 46 are not in contact with each other. In these examples, the reinforcements may be separated from one another by a separating structure, such as stitching, such that the position of each of the reinforcements is affixed in a position integral to the upper structure. Additionally or alternatively, the separating structure may permit either slight (less than 1 centimeter) lateral or longitudinal movement of the reinforcements while remaining integral to the upper structure. In some examples, each of the reinforcements may be secured in individual cavities of the upper structure and then secured in place with stitching such that the first reinforcement is separate from the third reinforcement and the second reinforcement is separate from the fourth reinforcement. In some examples, the third reinforcement and the fourth reinforcement are both comprised of a rigid material such that neither the third reinforcement nor the fourth reinforcement are capable of being bent. In some examples, the third reinforcement and the fourth reinforcement are both comprised of a flexible material such that each of the third reinforcement and the fourth reinforcement are capable of being bent while still providing a reinforcing effect. Additionally or alternatively, each of the third reinforcement and the fourth reinforcement are comprised of the same or a different material.

As shown in FIG. 2, each of the first reinforcement 24, second reinforcement 28, third reinforcement 44, and fourth reinforcement 46 has a reinforcement length $L_{24}$, $L_{28}$, $L_{44}$, and $L_{46}$, respectively, which extends parallel to the longitudinal axis $LA_{12}$. In addition, each of the first reinforcement 24, second reinforcement 28, third reinforcement 44, and fourth reinforcement 46 has a reinforcement width $W_{24}$, $W_{28}$, $W_{44}$, and $W_{46}$, respectively, which extends in a lateral direction. In some examples, the length of the third reinforcement 44 is less than the length of the first reinforcement 24, and the length of the fourth reinforcement 46 is less than the length of the second reinforcement 28. Additionally or alternatively, each of the first reinforcement, second reinforcement, third reinforcement, and fourth reinforcement may have equal widths or different widths. Additionally or alternatively, the widths of the first reinforcement, second reinforcement, third reinforcement, and fourth reinforcement may be constant (as shown in FIG. 2). Additionally or alternatively, the widths of the first reinforcement, second reinforcement, third reinforcement, and fourth reinforcement are variable at different portions along the lengths thereof. In some examples, and as shown in FIG. 2, the length of the first reinforcement 24 is equal to the length of the second reinforcement 28, and the length of the third reinforcement 44 is equal to the length of the fourth reinforcement 46. In some examples, the length of the first reinforcement 24 is different than the length of the second reinforcement 28, and the length of the third reinforcement 44 is different than the length of the fourth reinforcement 46.

In some examples, as shown in FIGS. 1 and 2, the brace 10 further comprises a fifth reinforcement 48 and a sixth reinforcement 50. The fifth reinforcement 48 is positioned laterally outward relative the third reinforcement 44, the first reinforcement 24, and the longitudinal axis $LA_{12}$ of the upper structure 12. The sixth reinforcement 50 is positioned laterally outward relative the fourth reinforcement 46, the second reinforcement 28, and the longitudinal axis $LA_{12}$. Each of the fifth reinforcement 48 and sixth reinforcement 50 are integral to the upper structure 12 and parallel to the longitudinal axis $LA_{12}$. Additionally or alternatively, the fifth reinforcement 48 is separate from the third reinforcement 44, and the sixth reinforcement 50 is separate from the fourth reinforcement 46 such that each of the fifth reinforcement 48 and third reinforcement 44 are not in contact with each other and that each of the sixth reinforcement 50 and fourth reinforcement 46 are not in contact with each other.

In these examples, the reinforcements may be separated from one another by a separating structure, such as stitching, such that the position of each of the reinforcements is affixed in a position integral to the upper structure. Additionally or alternatively, the separating structure may permit either slight lateral or longitudinal movement of the reinforcements while remaining integral to the upper structure. In some examples, each of the reinforcements may be secured in individual cavities of the upper structure and then secured in place with stitching such that the fifth reinforcement is separate from the third reinforcement and the sixth reinforcement is separate from the fourth reinforcement. In some examples, the fifth reinforcement and the sixth reinforcement are both comprised of a rigid material such that neither the fifth reinforcement nor the sixth reinforcement are capable of being bent. In some examples, the fifth reinforcement and the sixth reinforcement are both comprised of a flexible material such that each of the fifth reinforcement and the sixth reinforcement are capable of being bent. Additionally or alternatively, each of the fifth reinforcement and the sixth reinforcement are comprised of the same or a different material.

As shown in FIG. 2, each of the fifth reinforcement 48 and sixth reinforcement 50 has a reinforcement length $L_{48}$ and $L_{50}$, respectively, which extends parallel to the longitudinal axis $LA_{12}$ of the upper structure 12. In addition, each of the fifth reinforcement 48 and sixth reinforcement 50 has a reinforcement width $W_{48}$ and $W_{50}$, respectively, which extends in a lateral direction. In some examples, the length of the fifth reinforcement 48 is less than the length of the third reinforcement 44, which is less than the length of the first reinforcement 24. Additionally or alternatively, the length of the sixth reinforcement 50 is less than the length of the fourth reinforcement 46, which is less than the length of the second reinforcement 28. Additionally or alternatively, each of the first reinforcement, second reinforcement, third reinforcement, fourth reinforcement, fifth reinforcement, and sixth reinforcement may have equal widths or different widths. Additionally or alternatively, the widths of the first reinforcement, second reinforcement, third reinforcement, fourth reinforcement, fifth reinforcement, and sixth reinforcement may be constant (as shown in FIG. 2). Additionally or alternatively, the widths of the first reinforcement, second reinforcement, third reinforcement, fourth reinforcement, fifth reinforcement, and sixth reinforcement may be variable at different portions along the lengths thereof. In some examples, and as shown in FIG. 2, the length of the first reinforcement 24 is equal to the length of the second reinforcement 28, the length of the third reinforcement 44 is equal to the length of the fourth reinforcement 46, and the length of the fifth reinforcement 48 is equal to the length of the sixth reinforcement 50. In some examples, the length of the first reinforcement 24 is different than the length of the second reinforcement 28, the length of the third reinforcement 44 is different than the length of the fourth reinforcement 46, and the length of the fifth reinforcement 48 is different than the length of the sixth reinforcement 50.

In some examples in which the upper structure comprises a third reinforcement and a fourth reinforcement as well as a bracing component, such as is shown in FIGS. 1 and 2, the bracing component 36, which comprises a first end 38 and a second end 40, the first end 38 extends from the first lateral side 26 and the second end 40 is releasably secured to the second lateral side 30. As shown in FIGS. 1 and 2, the bracing component 36 is in-line with the third reinforcement 44, and the second end 40 is releasably secured to the second lateral side 30 in-line with the fourth reinforcement 46. In some examples, the bracing component is in-line with a different reinforcement on the first lateral side. Additionally or alternatively, the bracing component is not in-line with any reinforcement. In some examples, the second end is releasably secured to the second lateral side in-line with a different reinforcement on the second lateral side. Additionally or alternatively, the bracing component is not in-line with any reinforcement.

Figure 3:
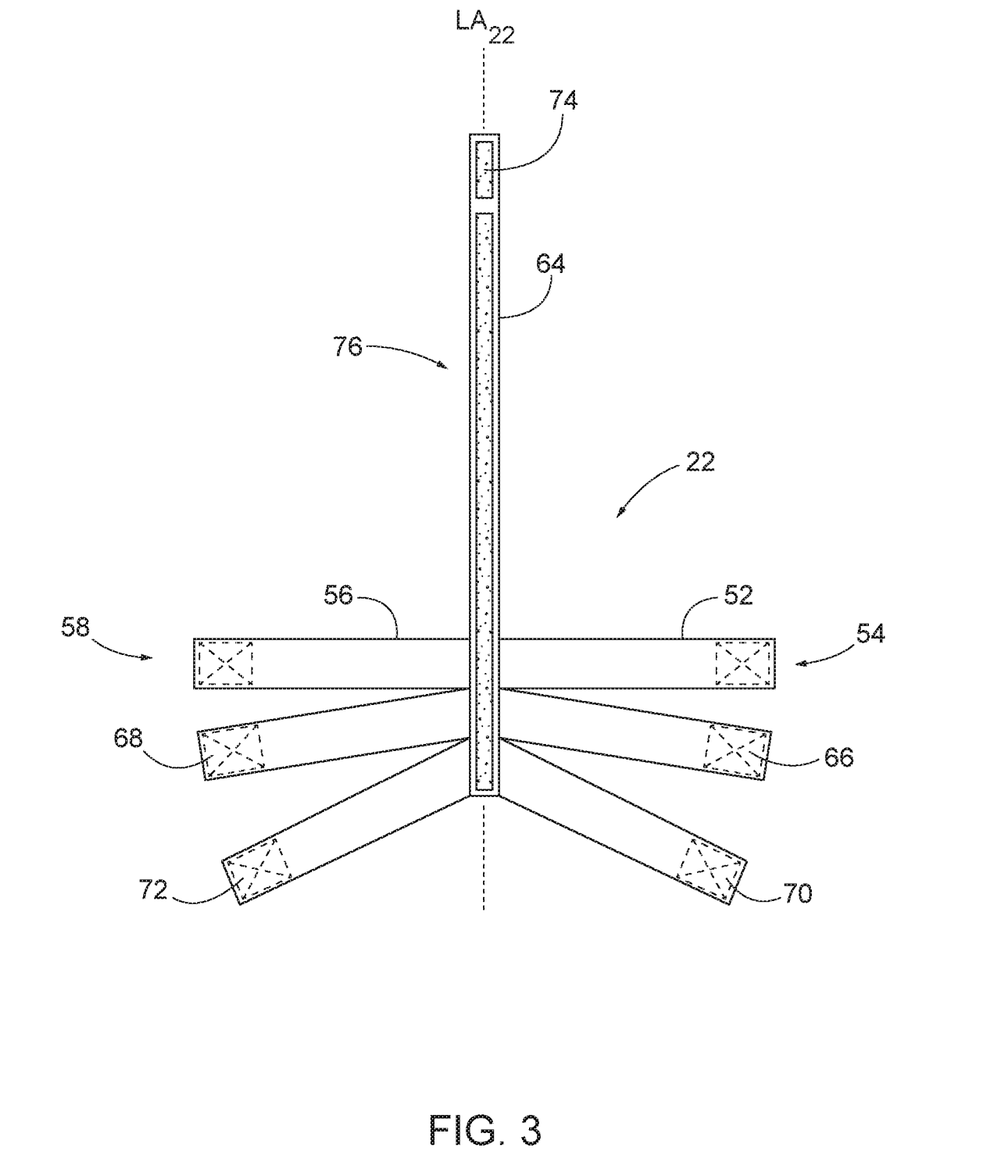
FIG. 3 is a bottom view of a lower structure of a back brace, in accordance with an example.
Figure 4:
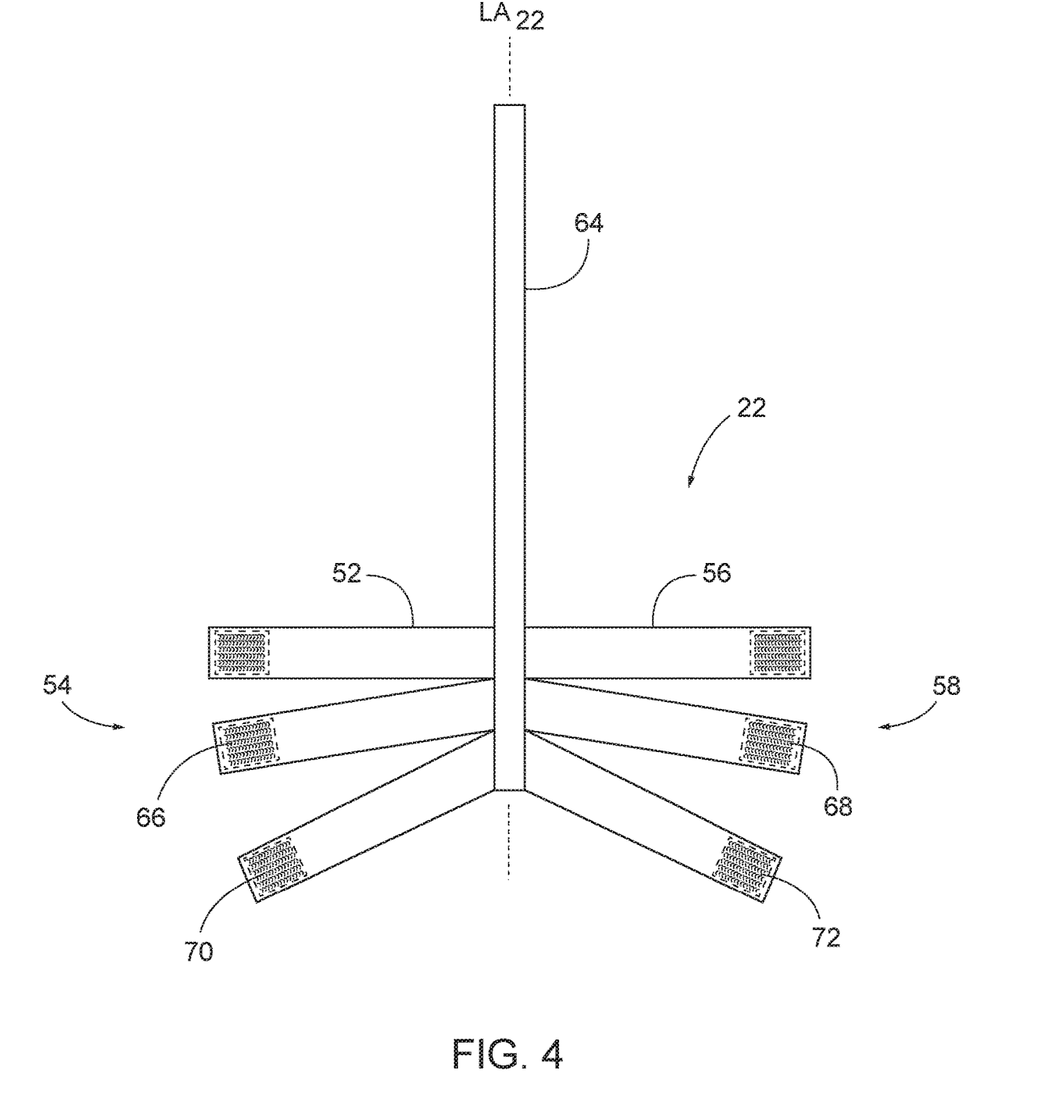
FIG. 4 is a top view of the lower structure of a back brace, in accordance with an example.
Figure 5:
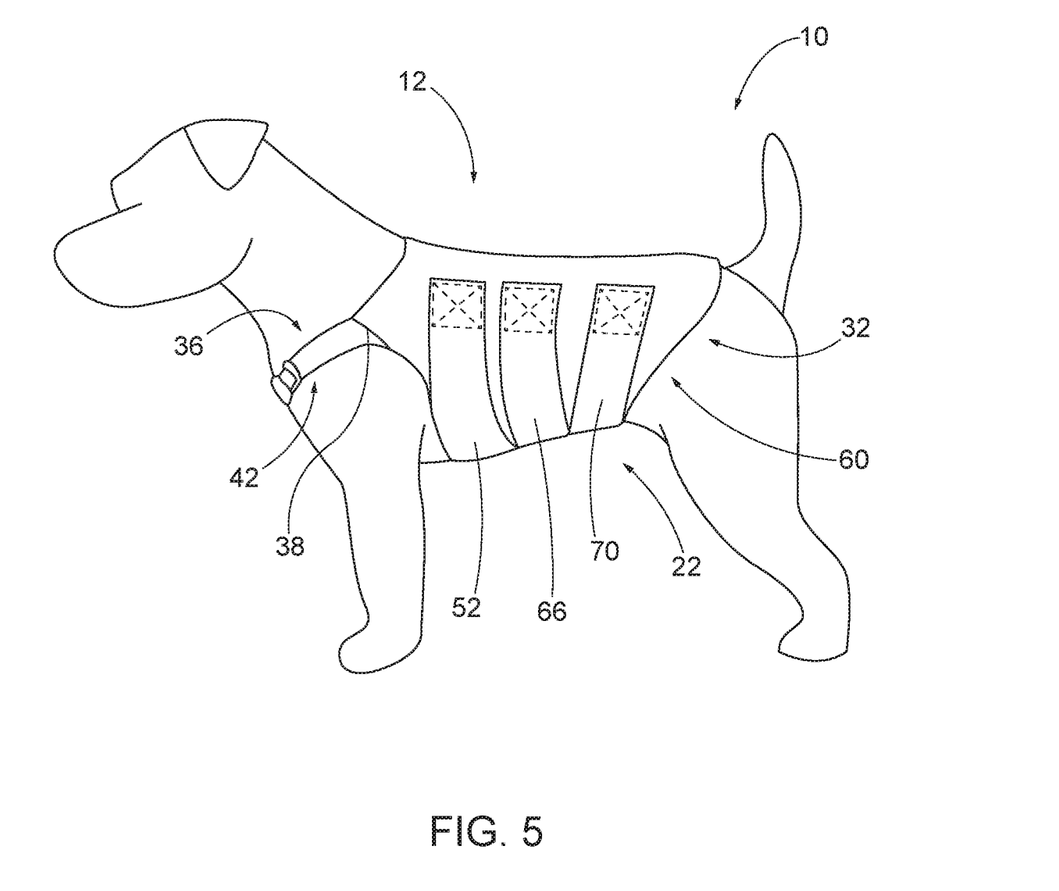
FIG. 5 is a left side view of a back brace in use on an animal, in accordance with an example.
Figure 6:
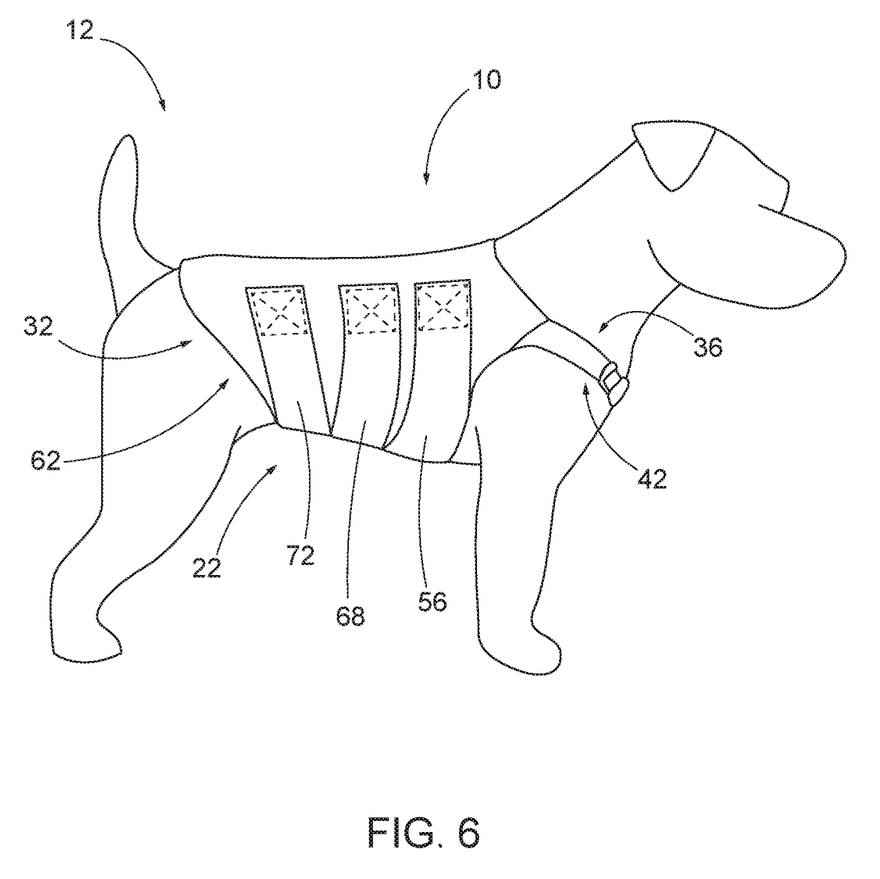
FIG. 6 is a right side view of a back brace in use on an animal, in accordance with an example.
Figure 7:
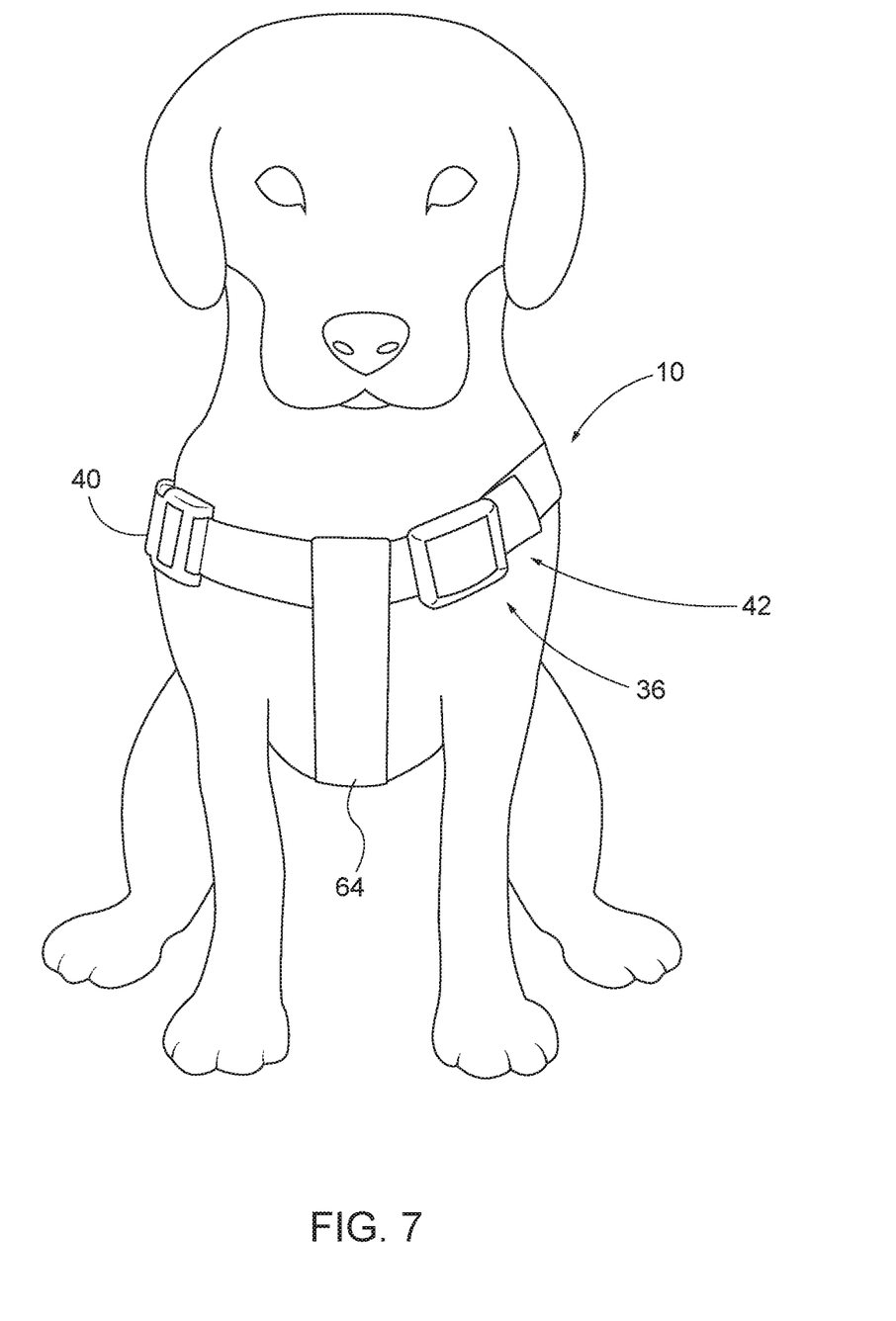
FIG. 7 is a front view of a back brace in use on an animal, in accordance with an example.

As shown in FIGS. 3 and 4, the lower structure 22 further comprises a first attachment component 52 positioned to a first lateral side 54 of a longitudinal axis $LA_{22}$ of the lower structure 22 and a second attachment component 56 positioned to a second lateral side 58 of the longitudinal axis $LA_{22}$ of the lower structure 22. Each of the first attachment component 52 and second attachment component 56 are releasably secured to a respective first attachment area 60 of the upper structure 12 and a respective second attachment area 62 of the upper structure 12. In some examples, the first attachment component is releasably secured to the first attachment area in-line with one of the reinforcements, and the second attachment component is releasably secured to the second attachment area in-line with another of the reinforcements. As shown in FIGS. 5 and 6, the first attachment component 52 is releasably secured to the first attachment area 60 in-line with the first reinforcement 24, and the second attachment component 56 is releasably secured to the second attachment area 62 in-line with the second reinforcement 28.

In some examples, such as those shown in FIGS. 3-6, the lower structure 22 further comprises a third attachment component 66 positioned to the first lateral side 54 of the longitudinal axis $LA_{22}$ of the lower structure 22 and a fourth attachment component 68 positioned to the second lateral side 58 of the longitudinal axis $LA_{22}$ of the lower structure 22. In some examples, as also shown in FIGS. 3-6, the lower structure 22 further comprises a fifth attachment component 70 positioned to the first lateral side 54 of the longitudinal axis $LA_{22}$ of the lower structure 22 and a sixth attachment component 72 positioned to the second lateral side 58 of the longitudinal axis $LA_{22}$ of the lower structure 22. In some examples, the third attachment component 66 is fanned outwardly from the first attachment component 52, and the fourth attachment component 68 is fanned outwardly from the second attachment component 56. Additionally or alternatively, the fifth attachment component 70 is fanned outwardly from both the third attachment component 66 and the first attachment component 52, and the sixth attachment component 72 is fanned outwardly from both the fourth attachment component 68 and the second attachment component 56. In various examples, each of the third and fourth attachment components and the fifth and sixth attachment components are fanned outwardly at identical angles. Moreover, in other examples, each of the third and fourth attachment components and the fifth and sixth attachment components are fanned outwardly at different angles. Additionally or alternatively, each of the attachment components is comprised of an elastic material to promote each of attachment to the attachment areas and comfort for the animal.

Figure 8:
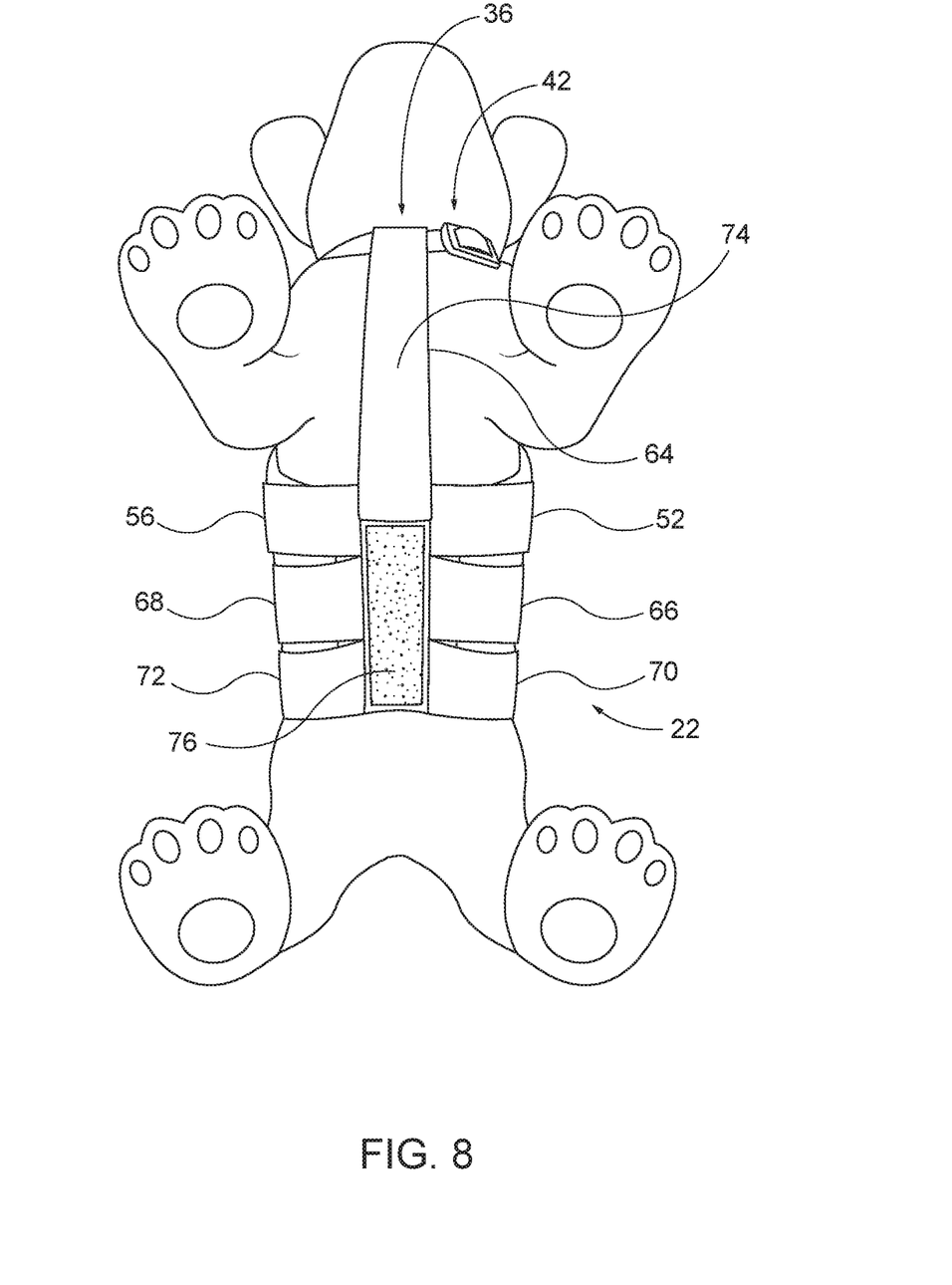
FIG. 8 is a bottom view of a back brace in use on an animal, in accordance with an example.

As shown in FIGS. 3 and 4, the lower structure 22 further comprises a longitudinal attachment component 64, which is secured to the adjustable attachment component of the bracing component of the upper structure. In some examples, as shown in FIGS. 3 and 4, the longitudinal attachment component 64 comprises a securing structure 74 and a receiving structure 76, where the securing structure 74 is releasably secured to the receiving structure 76. In various examples, as shown in FIG. 8, the longitudinal attachment component 64 loops around the adjustable attachment component 42 of the bracing component 36 such that the securing structure 74 is releasably secured to the receiving structure 76.

With specific reference to FIGS. 5-8, the brace 10 is shown in use on a dog. Some of the performance benefits of the brace 10 will now be described. When worn by a dog, any torquing movements or side-to-side movements by the dog are prevented since the reinforcements are each parallel to the longitudinal axis of the upper structure of the brace. In some examples, the longitudinal axis of the upper structure is parallel to the spine of the dog. Further, it is important that no reinforcement be located along the longitudinal axis of the upper structure, as the inclusion of a rigid material along the spine of the dog would further deteriorate and/or injure the already injured spine. Further, the fact that, in some examples, the reinforcements decrease in length along the side of the dog, being that the longest reinforcement is closest to the dog's spine, and the shortest reinforcement is furthest from the dog's spine further inhibits torquing or side-to-side movements, which helps to accelerate the healing of the injury. In addition, this arrangement allows for the body of the dog to support the spine in conjunction with the brace, which further aids the healing of the spine. Such an arrangement of the reinforcements also provides a comprehensive and universal fit, which allows for the longest and widest array of support. This is especially useful to treat diseases such as Intervertebral Disc Disease, which affects dogs of all sizes, shapes, and breeds.

With particular reference to the lower structure of the brace, the inclusion of multiple attachment components at multiple angles allows for a highly adjustable and customizable fit due to the fact that the upper structure has no specific and confined attachment areas. In addition, due to the elastic nature of the attachment components, the brace is able to fit a wider array of dogs with a variety of sizes. Still further, the exclusion of additional securing means, such as straps around a dog's legs, further aids in healing of the injury because a dog's leg will not need to be moved or lifted when securing the brace to the dog, which could further exacerbate an existing injury. Last, the inclusion of the longitudinal component, which may be releasably secured to the adjustable attachment component, allows for the spine of the dog to be further supported by the dog's shoulders through further weight distribution around the dog's shoulders.

The terms "comprising," "including," and "having," as used in the claims and specification herein, shall be considered as indicating an open group that may include other elements not specified. The terms "a," "an," and the singular form of words shall be taken to include the plural form of the same words, such that the terms mean that one or more of something is provided. The terms "at least one" and "one or more" are used interchangeably. The term "single" shall be used to indicate that one and only one of something is intended. Similarly, other specific integer values, such as "two," are used when a specific number of things are intended. The terms "preferably," "preferred," "prefer," "optionally," "may," and similar terms are used to indicate that an item, condition or step being referred to is an optional (i.e., not required) feature of the embodiments.

While this invention has been described with reference to embodiments thereof, it shall be understood that such description is by way of illustration only and should not be construed as limiting the scope of the claimed embodiments. Accordingly, the scope and content of the embodiments are to be defined only by the terms of the following claims.

Furthermore, it is understood that the features of any embodiment discussed herein may be combined with one or more features of any one or more embodiments otherwise discussed or contemplated herein unless otherwise stated.

What is claimed is:

1. A brace comprising:
   an upper structure having a length extending from a first longitudinal extent to a second longitudinal extent along a longitudinal axis and a width extending from a first lateral extent to a second lateral extent;
   a lower structure, where the lower structure is independent of the upper structure and is releasably secured to the upper structure;
   a first reinforcement positioned to a first lateral side of the longitudinal axis and a second reinforcement positioned to a second lateral side of the longitudinal axis, where the first reinforcement and the second reinforcement are integral to the upper structure and where the first reinforcement and the second reinforcement are parallel to the longitudinal axis;
   a third reinforcement positioned laterally outward relative the first reinforcement and the longitudinal axis and a fourth reinforcement positioned laterally outward relative the second reinforcement and the longitudinal axis, where the third reinforcement and the fourth reinforcement are integral to the upper structure and where the third reinforcement and the fourth reinforcement are parallel to the longitudinal axis; and
   the brace further comprising a fifth reinforcement positioned laterally outward relative the third reinforcement, the first reinforcement, and the longitudinal axis and a sixth reinforcement positioned laterally outward relative the fourth reinforcement, the second reinforcement, and the longitudinal axis, where the fifth reinforcement and the sixth reinforcement are integral to the upper structure and where the fifth reinforcement and the sixth reinforcement are parallel to the longitudinal axis;
   wherein, at least one of the first and second reinforcement, third and fourth reinforcement, or fifth and sixth reinforcement have both a first end that is offset along the longitudinal axis relative to an adjacent reinforcement and a second end opposite the first end and that is offset along the longitudinal axis relative to the adjacent reinforcement.

2. The brace of claim 1, where the upper structure further comprises a top side, the top side comprising a breathable material and a connecting material to which the lower structure is releasably secured.

3. The brace of claim 2, where the upper structure further comprises a bottom side comprising a breathable material.

4. The brace of claim 1, where the upper structure further comprises a bracing component, the bracing component comprising a first end and a second end, where the first end extends from the first lateral side and the second end is releasably secured to the second lateral side.

5. The brace of claim 4, where the bracing component further comprises an adjustable attachment component.

6. The brace of claim 5, the lower structure further comprises a first attachment component positioned to a first lateral side of a longitudinal axis of the lower structure and a second attachment component positioned to a second lateral side of the longitudinal axis of the lower structure, where each of the first and second attachment components are releasably secured to a respective first attachment area of the upper structure in-line with one of the reinforcements and a respective second attachment area of the upper structure in-line with another of the reinforcements, where the lower structure further comprises a longitudinal attachment component, where the longitudinal attachment component is secured to the adjustable attachment component.

7. The brace of claim 1, where the third reinforcement is separate from the first reinforcement and the fourth reinforcement is separate from the second reinforcement.

8. The brace of claim 1, where a length of the third reinforcement is less than a length of the first reinforcement and a length of the fourth reinforcement is less than a length of the second reinforcement, where the length of each of the reinforcements extends parallel to the longitudinal axis.

9. The brace of claim 1, where the lower structure further comprises a first attachment component positioned to a first lateral side of a longitudinal axis of the lower structure and a second attachment component positioned to a second lateral side of the longitudinal axis of the lower structure, where each of the first and second attachment components are releasably secured to a respective first attachment area of the upper structure in-line with one of the reinforcements and a respective second attachment area of the upper structure in-line with another of the reinforcements.

10. The brace of claim 9, where the lower structure further comprises a third attachment component positioned to the first lateral side of the longitudinal axis of the lower structure, a fourth attachment component positioned to the second lateral side of the longitudinal axis of the lower structure, a fifth attachment component positioned to the first lateral side of the longitudinal axis of the lower structure, and a sixth attachment component positioned to the second lateral side of the longitudinal axis of the lower structure, where third attachment component is fanned outwardly from the first attachment component, the fourth attachment component is fanned outwardly from the second attachment component, the fifth attachment component is fanned outwardly from both the third attachment component and first attachment component, and the sixth attachment component is fanned outwardly from both the fourth attachment component and the second attachment component.

11. The brace of claim 1, where a length of the fifth reinforcement is less than a length of the third reinforcement and a length of the sixth reinforcement is less than a length of the fourth reinforcement, where the length of each of the reinforcements extends parallel to the longitudinal axis.

12. The brace of claim 11, where the length of the third reinforcement is less than a length of the first reinforcement and the length of the fourth reinforcement is less than a length of the second reinforcement, where the length of each of the reinforcements extends parallel to the longitudinal axis.

13. The brace of claim 1, where each of the first reinforcement, second reinforcement, third reinforcement, and fourth reinforcement have a constant width, where the width of each of the reinforcements extends in a lateral direction.

14. The brace of claim 1, where each of the first reinforcement, second reinforcement, third reinforcement, fourth reinforcement, fifth reinforcement, and sixth reinforcement have a constant width, where the width of each of the reinforcements extends in a lateral direction.

15. The brace of claim 1, where the upper structure further comprises a bracing component comprising a first end and a second end, where the first end extends from the first lateral side and the second end is releasably secured to the second lateral side, where the bracing component is in-line with the third reinforcement.

16. The brace of claim 15, where the second end is releasably secured to the second lateral side in-line with the fourth reinforcement.

17. The brace of claim 1, where the fifth reinforcement is separate from the third reinforcement and the sixth reinforcement is separate from the fourth reinforcement.

18. A brace comprising:
an upper structure having a length extending from a first longitudinal extent to a second longitudinal extent along a longitudinal axis and a width extending from a first lateral extent to a second lateral extent;
a lower structure, where the lower structure is independent of the upper structure and is releasably secured to the upper structure;
a first reinforcement positioned to a first lateral side of the longitudinal axis and a second reinforcement positioned to a second lateral side of the longitudinal axis, where the first reinforcement and the second reinforcement are integral to the upper structure and where the first reinforcement and the second reinforcement are parallel to the longitudinal axis;
where the upper structure further comprises a bracing component, the bracing component comprising a first end and a second end, where the first end extends from the first lateral side and the second end is releasably secured to the second lateral side;
where the bracing component further comprises an adjustable attachment component;
a first attachment component positioned to a first lateral side of a longitudinal axis of the lower structure and a second attachment component positioned to a second lateral side of the longitudinal axis of the lower structure, where each of the first and second attachment components are releasably secured to a respective first attachment area of the upper structure in-line with one of the reinforcements and a respective second attachment area of the upper structure in-line with another of the reinforcements, where the lower structure further comprises a longitudinal attachment component, where the longitudinal attachment component is secured to the adjustable attachment component;
wherein, the longitudinal attachment component comprises a securing structure and a receiving structure, where the securing structure is releasably secured to the receiving structure.

\* \* \* \* \*